US005589932A

United States Patent [19]

Garcia-Rubio et al.

[11] Patent Number: 5,589,932
[45] Date of Patent: Dec. 31, 1996

[54] SPECTROPHOTOMETRIC METHOD AND APPARATUS FOR THE CHARACTERIZATION OF BLOOD AND BLOOD TYPES

[75] Inventors: Luis H. Garcia-Rubio, Temple Terrace; Manuel Bayona, Lutz; Robert Potter; German Leparc, both of Tampa, all of Fla.

[73] Assignee: University of South Florida, Tampa, Fla.

[21] Appl. No.: 385,717

[22] Filed: Feb. 8, 1995

[51] Int. Cl.[6] .............................. G01N 33/48; A61B 5/00; G06F 15/00
[52] U.S. Cl. ...................... 356/39; 128/633; 364/413.07; 364/413.08
[58] Field of Search ...................... 128/633; 364/413.07, 364/413.08; 356/39

[56] References Cited

U.S. PATENT DOCUMENTS

| | | | |
|---|---|---|---|
| 4,079,393 | 3/1978 | Al Marachy et al. | 356/39 |
| 4,223,680 | 9/1980 | Jöbsis | 128/633 |
| 4,281,645 | 8/1981 | Jöbsis | 128/633 |
| 4,655,225 | 4/1987 | Dähne et al. | 128/633 |
| 4,713,348 | 12/1987 | Ullman | 436/501 |
| 4,805,623 | 2/1989 | Jöbsis | 128/633 |
| 4,851,210 | 7/1989 | Hewett | 424/11 |
| 5,197,470 | 3/1993 | Helfer et al. | 128/634 |
| 5,259,382 | 11/1993 | Kronberg | 128/633 |
| 5,261,410 | 11/1993 | Alfano et al. | 128/664 |
| 5,341,805 | 8/1994 | Stavridi et al. | 128/633 |
| 5,377,674 | 1/1995 | Kuestner | 128/633 |

*Primary Examiner*—Frank Gonzalez
*Assistant Examiner*—Jason D. Eisenberg
*Attorney, Agent, or Firm*—Allen, Dyer, Doppelt, Franjola & Milbrath, P.A.

[57] ABSTRACT

A method and apparatus for determining the type of a blood sample are provided wherein a turbidity spectrum of the blood sample is collected over a predetermined wavelength range, from which is calculated an extinction spectrum. This extinction spectrum is then compared with a set of control spectra collected from control blood samples having known blood types, from which the type of the blood sample can be determined. A further method is provided for for detecting the presence of a substance in a bodily fluid sample, the substance having a size in the range of generally 0.5 to 20 µm. Exemplary substances that could be of interest to detect include, but are not limited to, hemoglobin, bilirubin, red blood cell antigens, microorganisms, and viruses. This embodiment includes the additional step of deconvoluting the extinction spectrum to obtain a particle size distribution for comparison with a database of control samples.

14 Claims, 5 Drawing Sheets

SPECTROPHOTOMETRIC METHOD AND APPARATUS FOR THE CHARACTERIZATION OF BLOOD AND BLOOD TYPES

BACKGROUND OF THE INVENTION

1. Field of the Invention

The present invention relates to the characterization of blood and other bodily fluids, and, more particularly, to the spectrophotometric characterization of blood types and other substances in the blood.

2. Description of Related Art

Current technology for blood typing or for the diagnosis of pathogens requires analysis by microscopy and/or immunoassay techniques. Specifically, for blood typing, an agglutination reaction is used that results from the association of specific antibodies with antigens present on the erythrocyte (red blood cell) surface. The disadvantages of this procedure are that they require significant amounts of time, trained individuals, and well-equipped laboratory facilities. For blood typing, for instance, an involved laboratory procedure is needed to detect the cell surface antigens.

Another limitation of the currently employed technology is a lack of on-line capability for the characterization of particles in bodily fluids, as well as a lack of portable instrumentation capable of detecting, counting, and classifying specific microorganisms, cells, and/or viruses of interest. The problem of portable instrumentation and suitable methods of analysis and diagnosis is particularly relevant to the medical industry, where the need for rapid analysis and diagnosis often involves life-threatening situations. Many times the need for portable instrumentation is further accentuated by the remoteness of the areas where epidemics often occur. Although the analytical instrumentation used in medical and clinical laboratories has improved considerably over the past decade, there are still no suitable techniques capable of detecting, classifying, and counting on-line critical cell populations and/or pathogens in bodily fluids. Typically the microorganisms and viruses of interest have sizes ranging between 0.5 and 20 μm, and, in many instances, are present in fairly dilute concentrations.

As is known from spectroscopy theory, a measure of the absorption of a solution is the extinction coefficient, which also provides a measure of the turbidity. Spectra in the visible region of the electromagnetic spectrum reflect the presence of metal ions and large conjugated aromatic structures double-bond systems. In the near-uv region small conjugated ring systems affect absorption properties. However, suspensions of very large particles are powerful scatterers of radiation, and in the case of microorganisms, the light scattering effect is sufficiently strong to obliterate absorption effects. It is therefore known to use uv/vis spectroscopy to monitor purity, concentration, and reaction rates of such large molecules.

Many attempts have been made to estimate the PSD and the chemical composition of suspended particles using optical spectral extinction (turbidity) measurements. However, previously used techniques require that either the form of the PSD be known a priori or that the shape of the PSD be assumed. The present inventor has applied standard regularization techniques to the solution of the turbidity equation and has demonstrated correct PSDs of a large variety of polymer lattices, protein aggregates, silicon dioxide particles, and microorganisms.

SUMMARY OF THE INVENTION

It is therefore an object of the present invention to provide a spectroscopic and turbidimetric technique for the characterization and differentiation of blood types.

It is a further object to provide such a technique for the rapid diagnosis of blood-borne pathogens.

It is another object to provide on-line instrumentation capable of rapid spectrophotometric blood typing.

It is an additional object to provide such instrumentation having at least 2 nanometer resolution.

It is another object to provide a technique capable of quantifying bodily fluid components, and, more particularly, blood components.

It is yet a further object to provide portable instrumentation capable of performing on-line analysis of bodily fluid components at remote locations.

These and other objects are addressed by the apparatus and method of the present invention for a method for determining the type of a blood sample. The method comprises the steps of collecting a turbidity spectrum of the blood sample over a predetermined wavelength range and calculating from the turbidity spectrum an extinction spectrum for the blood sample.

The next step comprises comparing the extinction spectrum with a set of control spectra collected from control blood samples, each control sample having a known blood type. Typically this set of control spectra will comprise a database of spectra collected from a large number of samples in order to provide adequate statistics for the comparison. From this comparison the type of the blood sample under study can be determined.

In the preferred embodiment of the method of the invention, the predetermined wavelength range comprises generally the ultraviolet-to-visible wavelength range, from 180 to 900 nm.

The apparatus of the present invention comprises means for performing the above-listed steps. In a particular embodiment, the spectrum collecting means comprises a spectrophotometer.

An additional embodiment of the present invention is a method for detecting the presence of a substance in a bodily fluid sample, the substance having a size in the range of generally 0.5 to 20 μm. Exemplary substances that could be of interest to detect include, but are not limited to, hemoglobin, bilirubin, red blood cell antigens, microorganisms, and viruses.

The method of this embodiment comprises the steps of collecting a turbidity spectrum over a predetermined range of wavelengths of the fluid sample and calculating from the turbidity spectrum an extinction spectrum. Next the extinction spectrum is deconvoluted to obtain a particle size distribution for the sample.

The extinction spectrum and the particle size distribution are then compared with, respectively, a control spectrum and a control particle size distribution for the substance. From these comparisons it can then be determined whether the organism to be detected is present in the sample.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

A description of the preferred embodiments of the present invention will now be presented with reference to FIGS. 1–8.

Figure 7:
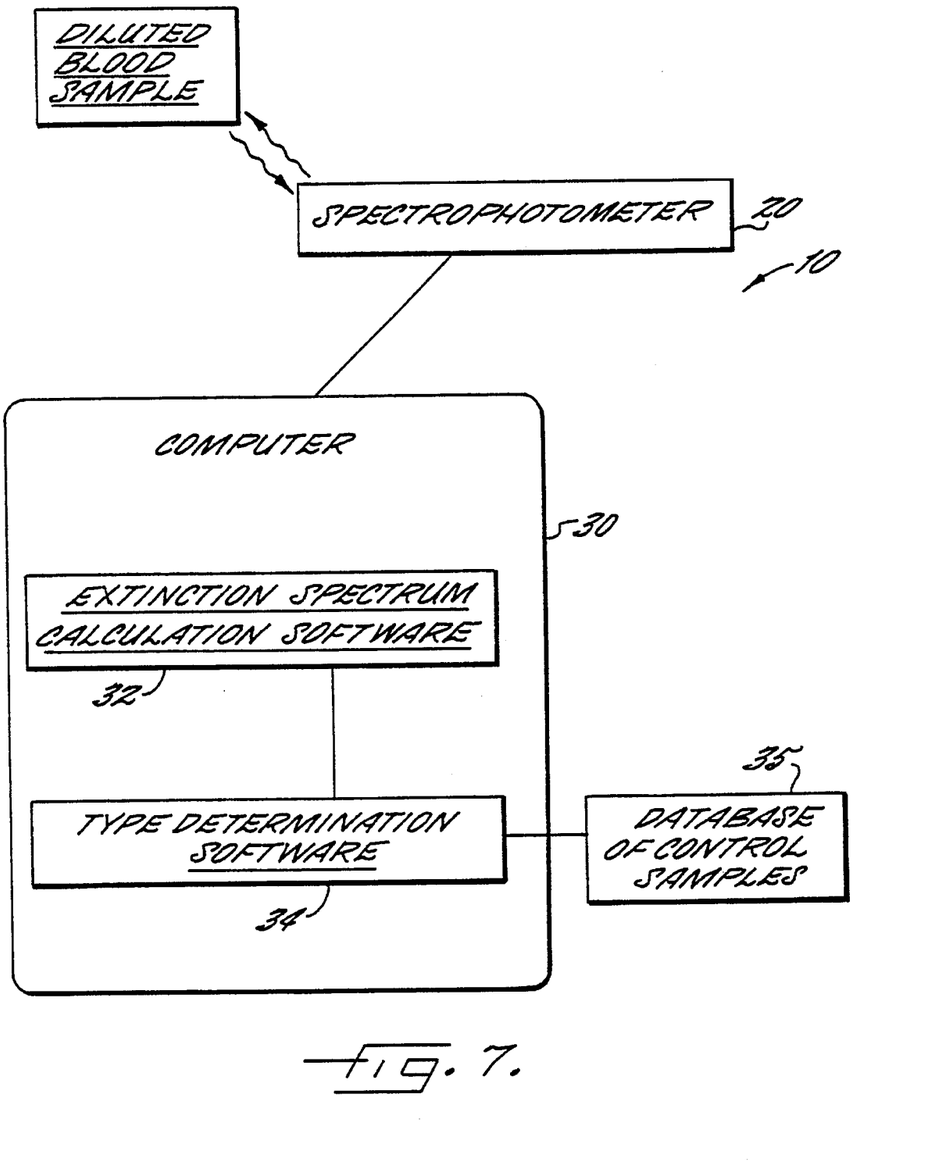
FIG. 7 is a block diagram of the system configuration.
Figure 8:
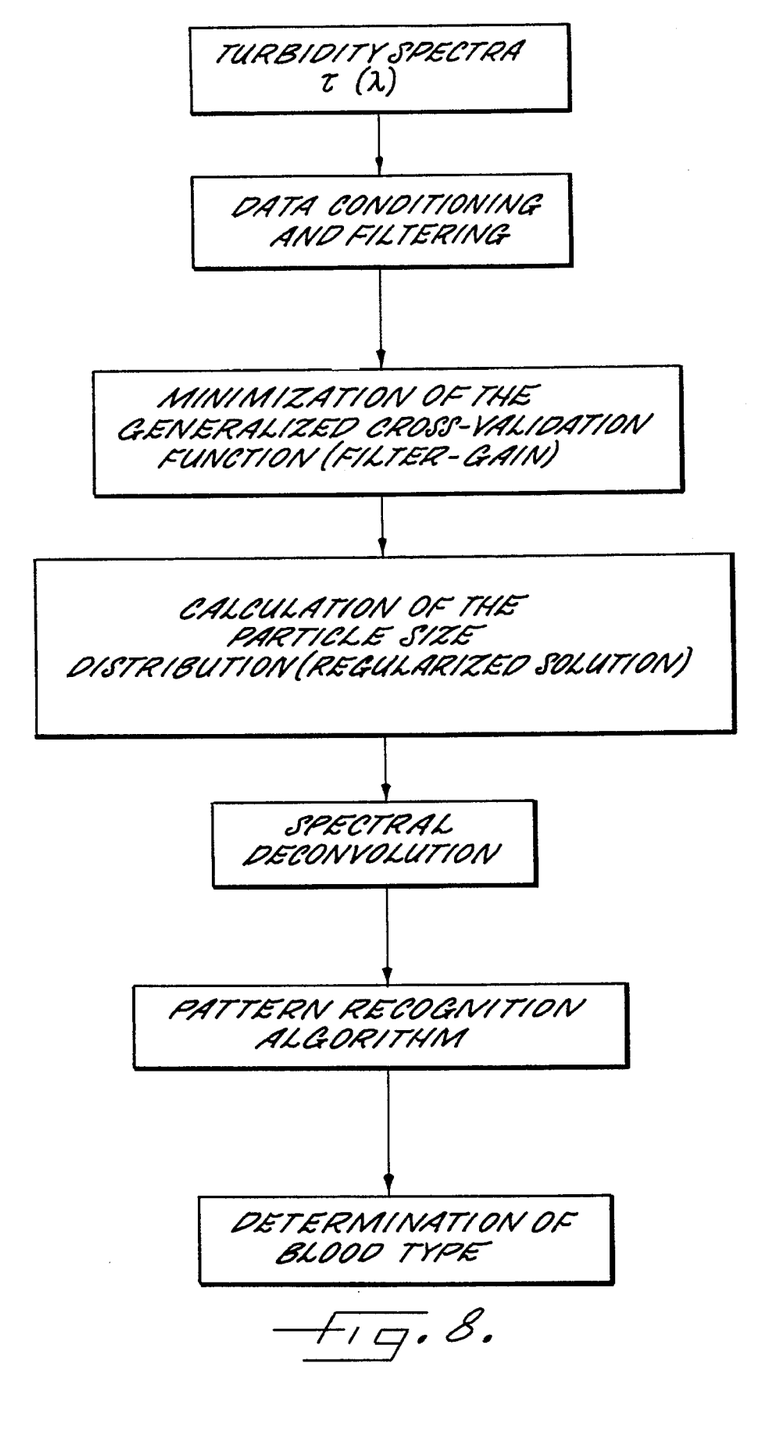
FIG. 8 is a flow chart of the data analysis method.

The apparatus 10 for determining the type of a blood sample are depicted in FIG. 7. This embodiment can be performed with portable equipment, and hence can serve as a rapid, on-line technique.

In the particular embodiment of the method to be treated herein, whole blood is used for the blood samples. Due to the optically dense nature of whole blood, considerable dilution is required prior to quantitative spectrophotometric measurements to reach a linear range of the spectrophotometer 20. Typically this is accomplished by serial dilution of the sample with phosphate buffered saline (PBS, 0.145M sodium chloride and 0.15M potassium phosphate, pH 7.2). The dilution in this embodiment consisted of first a 1:50 whole blood-to-PBS dilution followed by an additional 1:20 dilution of this solution into PBS. This resulted in a red blood cell count ranging from 3900 to 4100 per milliliter and an optical density of 0.1 to 1.0 absorption units, which is within the linear range of the instrument. This series of dilutions typically will result in a solution 22 that is in the linear range of the spectrophotometer used.

Using a spectrophotometer 20, such as a Hewlett Packard 8452A Diode Array Spectrophotometer, a turbidity spectrum of the blood sample 22 is collected over a predetermined wavelength range. In the preferred embodiment the predetermined wavelength range comprises generally the ultra-violet-to-visible (uv/vis) wavelength range, specifically, generally 180 to 820 nm, with a 2 nm resolution.

Using the turbidity spectrum thus obtained, which is recorded on a computer such as a Hewlett Packard Vectra 286/12 personal computer, an extinction spectrum is calculated using software developed by the inventors (see FIG. 8), illustrating the data analysis steps. This calculation further entails normalizing intensity effects due to the concentration of red blood cells in the blood sample.

The optical spectral extinction (turbidity) of a particle dispersion such as whole blood contains information that, in principle, can be used to estimate the particle size distribution (PSD) and the chemical composition of the suspended particles. The present inventors have devised a technique for determining a discretized particle size distribution from turbidity spectra. The equations providing the theoretical framework are developed from a relation between the turbidity as a function of wavelength $\tau(\lambda_0)$ and the normalized particle size distribution $f(D)$:

$$\tau(\lambda_0) = N_p(\pi/4) \int_0^\infty Q(\lambda_0, D) D^2 f(D) \, dD, \tag{1}$$

where $D$ is the effective particle diameter, $Q(\lambda_0,D)$ corresponds to the Mie scattering coefficient, and $N_p$ is the number of particles per unit volume. Equation (1) can be written in matrix form by discretizing the integral with an appropriate quadrature approximation:

$$\tau = A f + \epsilon, \tag{2}$$

where $\epsilon$ represents both experimental errors and errors due to the model and the discretization procedure. The regularized solution to Eq. (2) is given by:

$$f(\gamma) = (A^T A + \gamma H)^{-1} A^T \tau, \tag{3}$$

where $H$ is a covariance matrix that essentially adaptively filters the experimental and the approximation errors ($\epsilon$), and $\gamma$ is the regularization parameter estimated using the generalized cross-validation technique. This technique requires the minimization of the following objective function with respect to $\gamma$:

$$V(\gamma) = m\|[I - A(A^T A + \gamma H)^{-1}]\tau\|^2 / Tr\{[I - A(A^T A + \gamma H)^{-1}]A^T\}^2 \tag{4}$$

A simultaneous applications of Eqs. (3) and (4) to the measured turbidity spectra yields the discretized particle size distribution. Note that all the parameters required for the calculation of particle size distribution are obtained from the data. The corrected scattering spectra can then be used for composition analysis and/or to fingerprint the absorption characteristics of the blood components.

In order to calculate the error associated with the extinction spectra, five additional dilutions of the sample were measured. The first two dilutions involved addition of solvent to the cuvette (the measuring vial) followed by thorough mixing and measurement. The final two dilutions involved removal of a portion of the solution from the cuvette, followed by addition of solvent, thorough mixing, and measurement.

A database set of control spectra collected from control blood samples 35 was initially compiled by choosing samples of a specific gender and age range that are free of disease as judged by normal blood bank screening procedures. The control blood samples each have a known blood type. A complete database is contemplated as containing samples of both genders and a wide range of ages. The measurements reported herein are limited to females in the age range of 17 to 43 years. The broad age range used is because the rarer blood types make up a small percentage of the blood donor population and are difficult to obtain for analysis. The samples obtained include blood from the major eight blood types: A, B, AB, and O, both Rh positive and negative.

Figure 1:
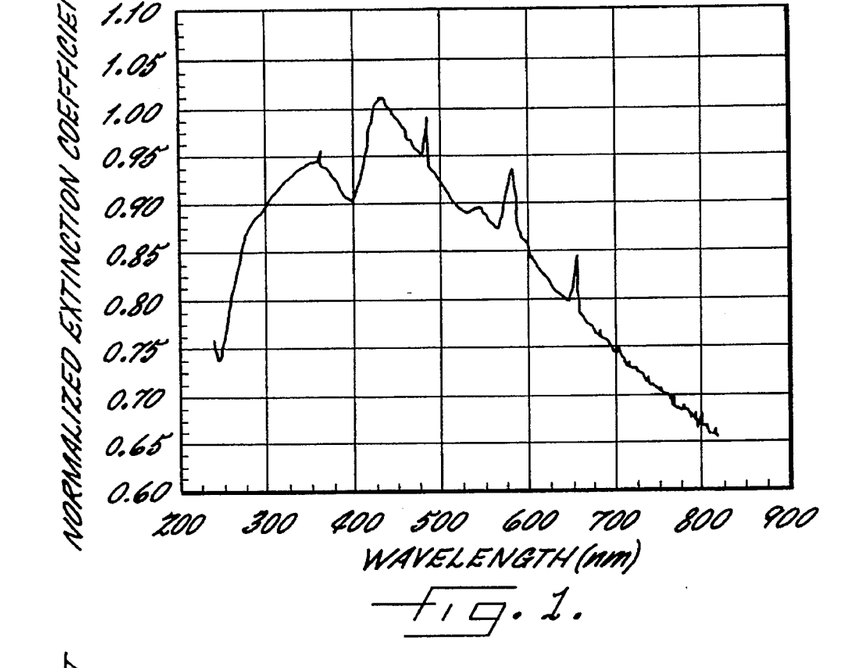
FIG. 1 shows a normalized extinction spectrum of a representative sample of A negative whole blood in phosphate buffered saline.
Figure 2:
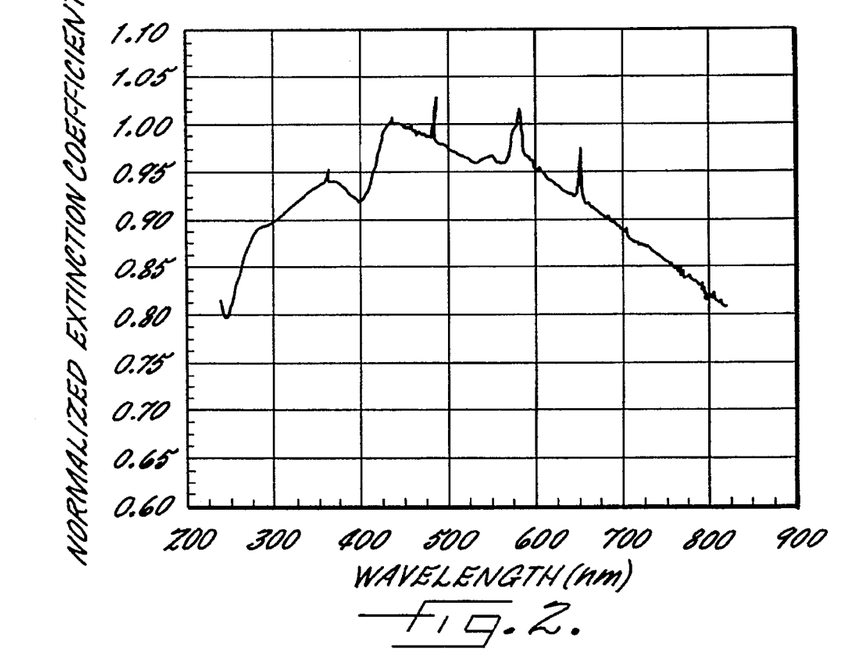
FIG. 2 shows a normalized extinction spectrum of a representative sample of O positive whole blood in phosphate buffered saline.
Figure 3:
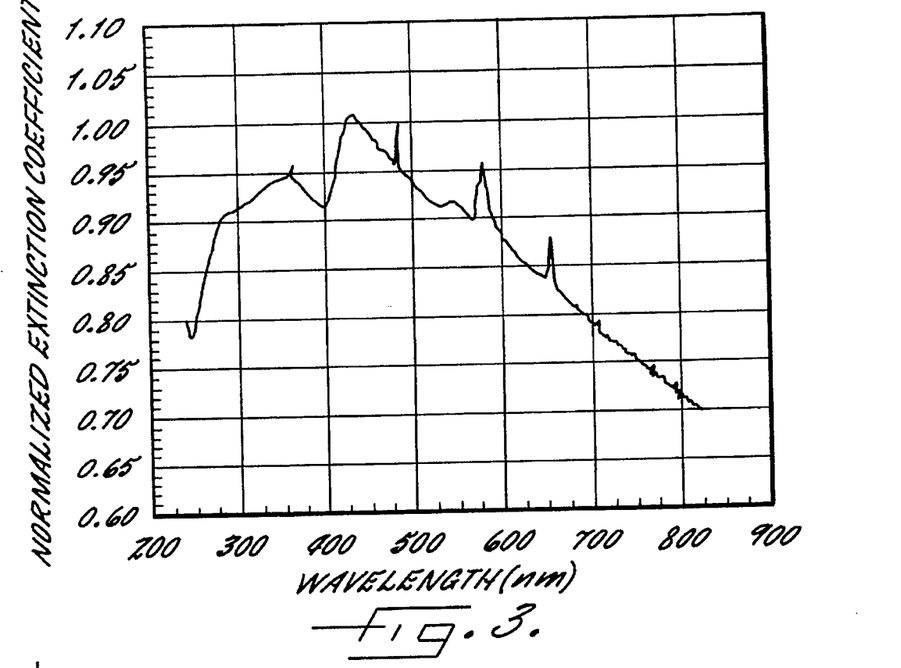
FIG. 3 shows a normalized extinction spectrum of a representative sample of AB positive whole blood in phosphate buffered saline.
Figure 4:
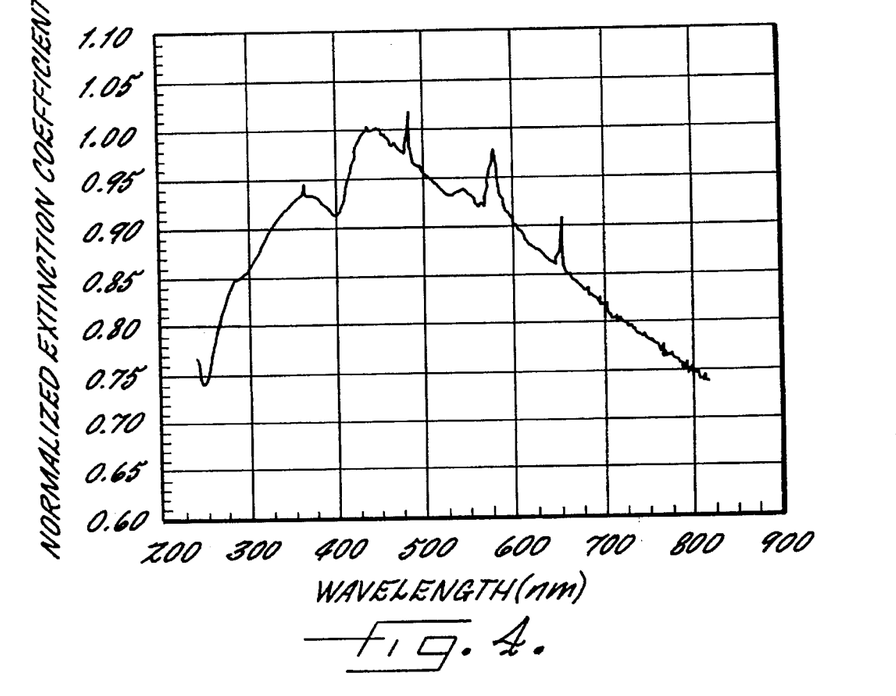
FIG. 4 shows a normalized extinction spectrum of a representative sample of B positive whole blood in phosphate buffered saline.
Figure 5:
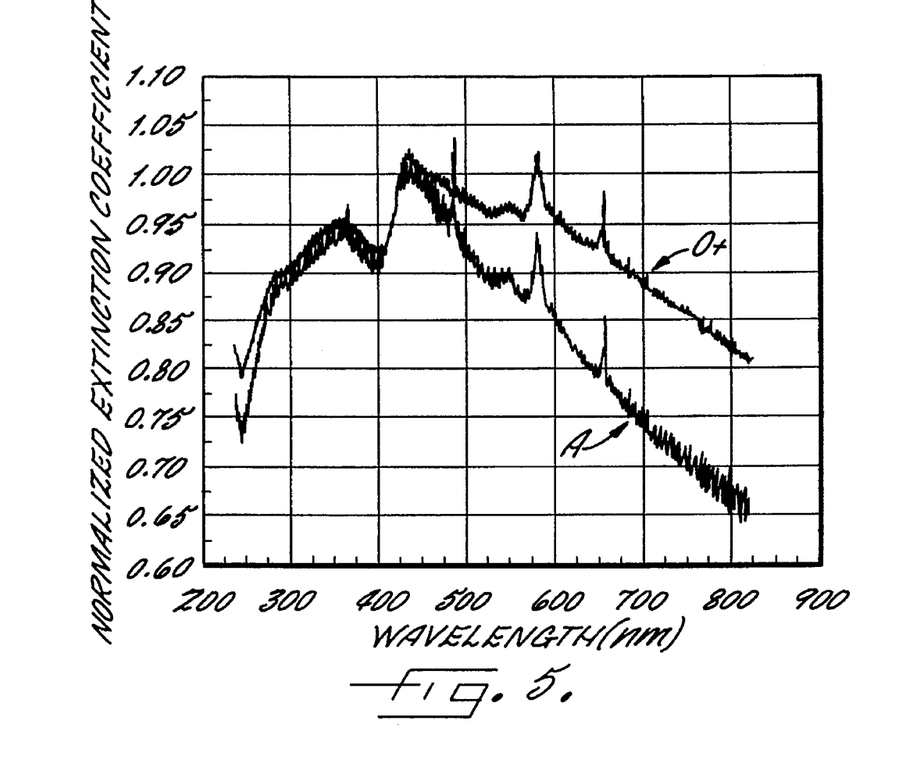
FIG. 5 shows typical 95% confidence intervals associated with the normalized extinction coefficients of two different blood samples. Error bars are indicative of the reproducibility of the experimental protocol.

In FIGS. 1–4, the normalized extinction spectra for representative samples of four of the eight different blood types are shown. FIG. 5 has the typical 95% confidence intervals superimposed on two different spectra to indicate the level of precision and the reproducibility of the experimental protocol.

Typing of a sample tan then be performed by comparing the extinction spectrum with the set of control spectra and determining from the comparison the type of the blood sample. Specifically, the typing is based on spectral differences that appear throughout portions of both the ultraviolet and visible range. At present the origin of these differences is unknown, but it may be due to intrinsic absorption differences at the molecular level or scattering differences brought about by either subtle variations in cell surface characteristics, cell shape, or state of aggregation.

A comparison of the spectra taken from samples of whole blood for different blood types (FIGS. 1–4) clearly indicates that, although the spectra are generally similar in that they contain the same peaks and troughs, the underlying structure and the relative peak intensities are consistently and significantly different. Furthermore, a statistical analysis of the samples also suggests that the blood types are spectrally distinguishable. Therefore, it can be concluded that the uv/vis portion of the spectrum contains sufficient information for the statistical identification and classification of blood types.

In order to test one aspect of the origin of differences in samples of different blood types, turbidity spectra were collected on lysed red blood cell samples. The procedure for this test included dilution with two different hypotonic solvents, 0.3 and 0.4% buffered NaCl, chosen to be sufficiently hypotonic to lyse the red blood cells.

Figure 6:
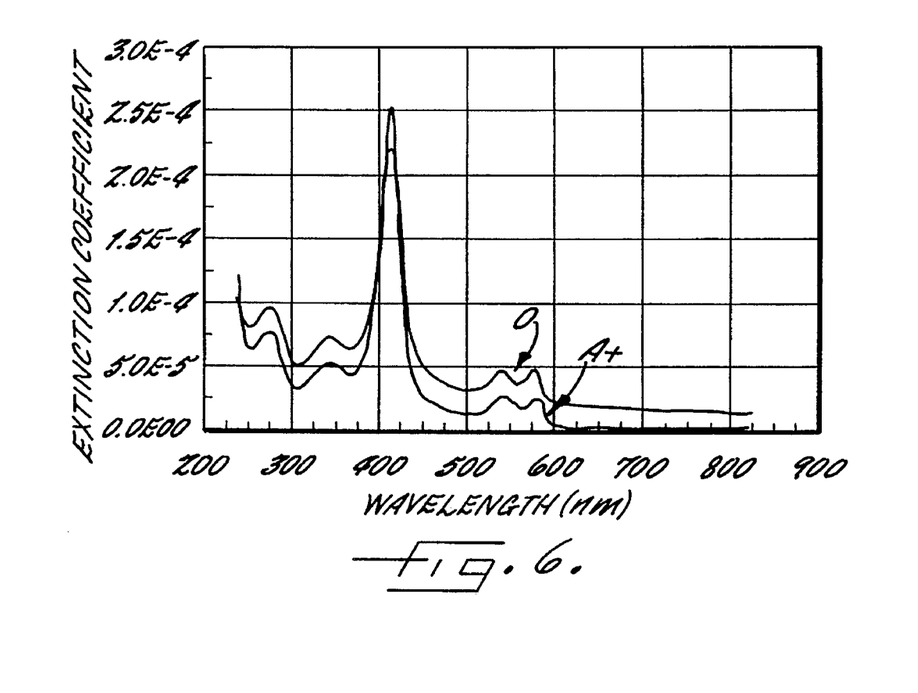
FIG. 6 shows extinction spectra of lysed O negative and A positive red blood cells. Cells were lysed by suspension in hypotonic saline solution (A positive in 0.3% and O negative in 0.4% buffered NaCl).

FIG. 6 shows spectra taken from two lysed blood specimens, specifically O negative and A positive types. A comparison of FIGS. 1–4 with the spectra of the red blood cell components in FIG. 6 shows clear and significant differences between these samples. It can be noted that the spectra for the lysed cell samples are quite similar to each other; that is, the number of peaks, peak positions, and relative intensities are the same for the two distinct blood types once they have been lysed. Therefore, the differences observed between blood types appear to be due to cell size or one or more components of the whole cell structure rather than gross chemical composition. Similar conclusions can be drawn from spectra collected from plasma, which are almost identical regardless of the differences in the whole blood type from which they came.

A further aspect of the present invention is an apparatus 10 for determining the type of a blood sample (see FIG. 7). The apparatus in general comprises means for performing the steps of the above-discussed method. In the preferred embodiment, the apparatus 10 includes a spectrophotometer 20 for collecting spectra in the predetermined wavelength range of generally 180 to 800 nm with a resolution of 2 nm, the sample 22 having been sufficiently diluted to reach a linear range of the spectrophotometer.

Additionally, the calculating means comprises software means resident in a computer 32 for calculating an extinction spectrum from the turbidity spectra and software 34 for determining a blood type from a comparison with the database 35.

In yet another embodiment, a method is provided for detecting the presence of a substance in a bodily fluid sample, the substance having a size in the range of generally 0.5 to 20 μm. Exemplary substances that could be of interest to detect include, but are not limited to, hemoglobin, bilirubin, red blood cell antigens, microorganisms, and viruses. The method generally comprises the steps of collecting a turbidity spectrum over a predetermined range of wavelengths of the fluid sample and calculating from the turbidity spectrum an extinction spectrum.

The method further entails deconvoluting the extinction spectrum to obtain a particle size distribution for the sample, as outlined in the above discussion on the turbidity equations. The extinction spectrum and the particle size distribution are then compared with, respectively, a control spectrum and a control particle size distribution for the substance, and it can then be determined from the comparisons whether the organism to be detected is present in the sample. Another application includes a further step, to determine the quanitity of the substance to be detected in the fluid sample from the particle size distribution.

In order to accomplish the foregoing, an additional series of databases must be compiled for each of the components of interest. A quantitative identification of the blood components and the generation of an adequate database allows for the subsequent identification of blood abnormalities such as those brought about by bacterial or viral infections by comparison with the spectral signature of normal blood, and by differences in the cell size distribution calculated from the same measurement.

For a more detailed characterization, these spectra can be further analyzed in conjunction with other currently employed technologies, such as dynamic light scattering, in order to estimate the number as well as the complete size distribution of the components of interest according to size and chemical composition.

It may be appreciated by one skilled in the art that additional embodiments may be contemplated, including systems and methods for characterizing other bodily fluids and their constituents, such as, but not limited to, saliva and spinal fluid.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A method for determining the type of a blood sample, the method comprising the steps of:

collecting a turbidity spectrum of the blood sample over a predetermined wavelength range;

calculating from the turbidity spectrum an extinction spectrum for the blood sample;

comparing the extinction spectrum with a set of control spectra collected from control blood samples, each control sample having a known blood type; and determining from the comparison the type of the blood sample.

2. The method for determining the type of a blood sample recited in claim 1, wherein the calculating step further comprises the step of normalizing intensity effects due to a concentration of red blood cells in the blood sample.

3. The method for determining the type of a blood sample recited in claim 1, wherein the predetermined wavelength range comprises the ultraviolet-to-visible wavelength range.

4. The method for determining the type of a blood sample recited in claim 3, wherein the ultraviolet-to-visible wavelength range comprises a wavelength range of 180 to 820 nm.

5. The method for determining the type of a blood sample recited in claim 4, wherein the collecting step further comprises collecting the turbidity spectrum with a 2 nm resolution.

6. The method for determining the type of a blood sample recited in claim 1, wherein the collecting step comprises collecting the turbidity spectrum with a spectrophotometer.

7. The method for determining the type of a blood sample recited in claim 6, further comprising the step, prior to the collecting step, of diluting the blood sample sufficiently to reach a linear range of the spectrophotometer.

8. An on-line method for spectrophotometrically determining the type of a whole blood sample, the method comprising the steps of:

diluting the blood sample with phosphate buffered saline to reach a red blood cell concentration in the range of 3900–4100 per milliliter and an optical density of 0.1 to 1.0 absorbance units in order to reach a linear range of the spectrophotometer;

collecting a turbidity spectrum of the blood sample with the spectrophotometer over a wavelength range of 180–820 nm with a resolution of 2 nm;

calculating from the turbidity spectrum an extinction spectrum for the blood sample, the calculation including a normalization of intensity effects due to the red blood cell concentration;

comparing the extinction spectrum with a set of control spectra collected from control blood samples, each control sample having a known blood type; and determining from the comparison the type of the blood sample.

9. An apparatus for determining the type of a blood sample, the apparatus comprising:

means for collecting a turbidity spectrum of the blood sample over a predetermined wavelength range;

means for calculating from the turbidity spectrum an extinction spectrum for the blood sample;

means for comparing the extinction spectrum with a set of control spectra collected from control blood samples, each control sample having a known blood type; and means for determining from the comparison the type of the blood sample.

10. The apparatus recited in claim 9, wherein the collecting means comprises a spectrophotometer.

11. The apparatus recited in claim 10, wherein the predetermined wavelength range comprises 180 to 800 nm.

12. The apparatus recited in claim 11, wherein the the spectrophotometer has sufficient sensitivity to collect the turbidity spectrum with a resolution of 2 nm.

13. The apparatus recited in claim 11, further comprising means for diluting the blood sample for reaching a linear range of the spectrophotometer.

14. The apparatus recited in claim 10, wherein the calculating means comprises a computer adapted to receive the tubidity spectrum from the spectrophotometer and software means for calculating an extinction spectrum from the turbidity spectrum resident in the computer.

\* \* \* \* \*

UNITED STATES PATENT AND TRADEMARK OFFICE
CERTIFICATE OF CORRECTION

| | | |
|---|---|---|
| PATENT NO. | : | 5,589,932 |
| DATED | : | December 31, 1996 |
| INVENTOR(S) | : | Garcia-Rubio, et al |

It is certified that error appears in the above-identified patent and that said Letters Patent is hereby corrected as shown below:

Column 1, Line 9     Insert::

This invention was made with U. S. Government support under NSF Grant RII-850-756 awarded by the Department of the Navy. The Government has certain rights in the invention.- -

Signed and Sealed this

Third Day of March, 1998

Attest:

BRUCE LEHMAN

Attesting Officer

Commissioner of Patents and Trademarks